United States Patent [19]

Scholz

[11] Patent Number: 4,457,176

[45] Date of Patent: Jul. 3, 1984

[54] NON-DESTRUCTIVE METHOD AND DEVICE FOR ULTRASONIC TESTING OF THE MATERIAL OF GENERATOR ROTOR TEETH

[75] Inventor: Arthur Scholz, Wettingen, Switzerland

[73] Assignee: BBC Brown, Boveri & Company, Limited, Baden, Switzerland

[21] Appl. No.: 381,832

[22] Filed: May 25, 1982

[30] Foreign Application Priority Data

Jun. 11, 1981 [CH] Switzerland .......................... 3823/81

[51] Int. Cl.³ ............................................. G01N 29/04
[52] U.S. Cl. ........................................ 73/624; 73/625; 73/628
[58] Field of Search ................ 73/620, 624, 625, 626, 73/627, 628, 629, 641

[56] References Cited

U.S. PATENT DOCUMENTS 3,962,908 6/1976 Joy ........................................ 73/641

Primary Examiner—James J. Gill

Attorney, Agent, or Firm—Oblon, Fisher, Spivak, McClelland & Maier

[57] ABSTRACT

A process and a device for the nondestructive ultrasonic testing of the material of generator rotor teeth providing with an inserted slot wedge, using a probe arrangement including transmit probes, reference probes and defect detection probes which are disposed on a support plate in such a manner as to be movably attached to the teeth, wherein ultrasonic beams are transmitted and reflected by the rotor teeth flanks and the reflected beams are received in a reference probe utilizing a two-fold deflection of the sound at the tooth flanks which are inclined with respect to the tooth back. An ultrasonic beam, reflected by any existing defects of a given type and orientation, is selectively received outside the receiving range of the normally reflected acoustic beam by means of a defect detection probe, and the damaged locations is detected by comparison of the ultrasonic signals received by the reference and defect detection probes. Defects can be properly identified in rotor teeth having differing tooth flank angles by means of the two-fold beam deflection at the tooth flanks, and also with the use of additional reference probes.

5 Claims, 7 Drawing Figures

NON-DESTRUCTIVE METHOD AND DEVICE FOR ULTRASONIC TESTING OF THE MATERIAL OF GENERATOR ROTOR TEETH

BACKGROUND OF THE INVENTION

1. Field of the Invention:

The invention relates to a method and a device for the nondestructive material testing by means of ultrasonics on generator rotor teeth having an inserted slot wedge therebetween, using at least one transmit probe and at least one receive probe.

2. Description of the Prior Art:

Generator rotor teeth consist of high-tensile steel and are subjected during operation to a consistently high mechanical loading by forces acting in the axial and radial directions and resulting, on the one hand, from the so-called alternation of rotational load and, on the other hand, from the contact pressure of the slot wedges against the rotor teeth flanks.

Under unfavorable conditions and with the additional occurence of frictional corrosion at the areas of contact between the slot wedge and the rotor tooth, fatigue cracks can form which originate from these contact areas. These fatigue cracks are always oriented vertically with respect to the rotor axis and, under the above-mentioned mechanical stresses, can continue to grow after a certain critical crack depth has been reached. These defects in the rotor teeth would present a considerable safety hazard for the operation of the electric machine. For this reason, a regular check of rotor teeth is very important. In order to avoid high disassembly and assembly costs and prolonged outages of the electric machine, the rotor teeth are tested in the wedge-slot condition.

For this test, the nondestructive ultrasonic method of testing materials is advantageously used.

In the "Technical Disclosure Bulletin" of the "Central Electricity Generating Board, London," No. 330, of July 1979, entitled "The In-Situ Ultrasonic Examination of Large Generator Rotors," such a test method is described and illustrated. However, this test method can apparently only be used to test rotor teeth where the wedge support areas or tooth flanks, respectively, run parallel to the tooth backs of the rotor teeth.

Most of the rotor designs, however, have wedge support areas which are not parallel to the tooth backs of the rotor teeth but which normally form an angle of 40°-70° with the vertical of the rotor tooth neck. The above-mentioned test method cannot be used for this type of rotor design.

SUMMARY OF THE INVENTION

Accordingly, one object of this invention is to provide a novel method and device for nondestructive material testing of generator rotor teeth, using ultrasonics, which remedies the above-noted deficiency in the prior art.

This and other objects are achieved by providing a novel method for the nondestructive ultrasonic testing of materials on generator rotor teeth provided with an inserted slot wedge and having differing flank and crest angles of the rotor teeth, wherein an ultrasonic beam is radiated and directed by a transmit probe to be firstly reflected at a tooth flank and then at the opposite tooth flank of the same rotor tooth, and the acoustic beam reflected from the second tooth flank is received in a reference probe and signalled. Outside the receiving range of the normally reflected ultrasonic beam an ultrasonic beam reflected by any existing defects of a given type and orientation is selectively received by means of a defect detection probe and the damaged points are detected.

This test method of the invention has the following advantages:

reliable testing of the wedge support areas, which are inclined with reference to the tooth neck, with slot wedge inserted becomes only possible, in the first instance, by double deflection of the acoustic beam;

by using a reference probe, especially the acoustic beam losses caused by the wedge contact pressure can be taken into consideration during defect analysis which makes for more precise defect detection with respect to defect size; and the way of directing the acoustic beam according to the invention results in high selectivity and thus a large error signal/background noise ratio in the detection of defects of the type and orientation encountered in the case of rotor teeth.

In the same way, the use of a reference receiver makes it possible to pay appropriate attention to the acoustic beam losses which can arise as a result of improper probe-to-specimen contact on transition from the probes into the specimen and vice versa.

By comparing signals from the reference probe and the defect detection probe, the extent of the damaged locations and orientation of the defect type searched for are detected. This comparison is carried out in an automatic analysis system and defect detection thus takes place in a simple and rapid manner.

Plural probes can be provided whereby a probe can be used both as a transmit probe and, for another probe, as a reference probe, the respective operating mode, transmitting or receiving, being determined by an electric clock generator. In addition, each tooth flank can be associated with a respective defect detection probe. With this probe arrangement, two tooth flanks can be simultaneously tested with one test operation by adding only one more probe to the already existing three.

According to the invention, the probes are arranged on a support plate in such a manner as to be movably attached, and are adjusted to the flank angles and crest angles and thus also to the width of the rotor teeth by being rotated out laterally. The contact area of the support plate, in turn, matches the surface of the rotor teeth. As a result of this design measure, the probes are made to fit the geometric shape of the rotor teeth by simple adjustment of the probes without any additional mechanical devices.

Further according to the invention, the transmit probe, reference probe and defect detection probe are arranged at a spatial distance from one another in the longitudinal and circumferential directions of the rotor.

Still further according to the invention, in each case one transmit probe and one reference probe, although spatially arranged at a distance from one another in the longitudinal and circumferential direction of the rotor, form one functional unit and work in conjunction with one another in such a manner that each probe alternately works as a transmitter or as a receiver.

In one embodiment of the invention, one reference probe and one defect detection probe form one probe unit which works in conjunction with two transmit probes, the probe unit and the two transmit probes being arranged spatially at a distance from one another in the longitudinal and circumferential directions of the rotor.

In another embodiment, the transmit probe and the defect detection probe form one probe unit and work in conjunction with one reference probe, the probe unit and the reference probe again being arranged spatially at a distance from one another in the longitudinal and circumferential directions of the rotor.

Still further according to the invention, the above noted support plate is arranged in the longitudinal direction of the generator rotor tooth and can be moved from one to the opposite face of the rotor and is supported on these faces.

In another embodiment, the support plate is provided with at least two magnets which act in conjunction with the tooth surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
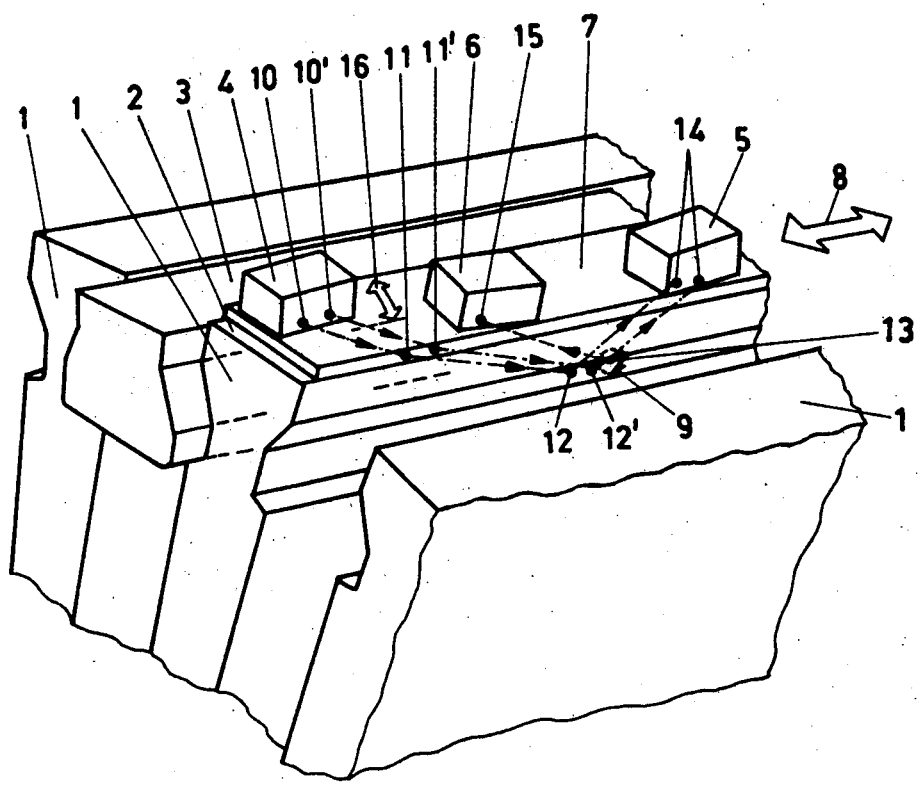
FIG. 1 is a perspective view of a part of a rotor.

Referring now to the drawings, wherein like reference numerals designate identical or corresponding parts throughout the several views, and more particularly to FIG. 1 thereof, FIG. 1 shows a part of a rotor in which on the crest 2 of the rotor tooth 1 a transmit probe 4, a reference probe 5 and a defect detection probe 6 are arranged which are supported by a support plate 7. This support plate 7 matches the shape of the crest 2 of the rotor tooth 1.

FIG. 1 also shows a slot wedge 3 so that it can be seen that the test can also take place without disassembly of the slot wedges 3. However, the slot wedge 3 between the middle and front rotor teeth 1 has not been drawn so that the path of the ultrasonic beam in the rotor tooth 1 can be shown more clearly. Reference number 8 designates the direction of movement of the support plate 7 which can be manually or mechanically moved in the axial direction over the total length of the rotor tooth 1 from one face of the rotor to the other.

By way of example, in rotor tooth 1 a defect 9 is shown. The existence and position of defect 9 is to be determined by ultrasonic testing determination of the point(s) at which the ultrasonic beam is partially reflected.

The path of the ultrasonic beam, radiated and directed by the transmit probe 4, through the rotor tooth 1 to be tested is initially described for the non-defective condition of the rotor tooth 1, only the beam axis being shown in each case. The axis of the ultrasonic beam emerges from the transmit probe 4 at the point designated by reference number 10, penetrates the support plate 7, impinges on the left-hand flank of the rotor tooth 1 at point 11, is reflected from there and impinges on the right-hand flank of the rotor tooth 1 at point 12. Since no defect 9 is located in the path of the ultrasonic beam in the example shown, the beam is reflected directly into the reference receiver 5 which signals that the rotor tooth 1 has no defects.

The high-frequency cable, required for the generation and reception of the ultrasonic waves, on the probes 4, 5, and 6 are not shown for the sake of clarity.

When the support plate 7 is then moved to the right along the direction of the arrow (8) (for the sake of clarity, the housings of the probes 4, 5, and 6, and hence also the support plate 7 are shown at their original place, and only the path of the ultrasonic beam is shown varied), the ultrasonic beam, for example then emitted and directed by the transmit probe 4, emerges from the latter at the point 10', again first penetrates the support plate 7, impinges on one flank of the rotor tooth 1 at the point 11', is reflected from there, impinges on the other flank of the rotor tooth 1 at the point 12' and is again reflected from there. The radiation beam is now split by a defect 9 so that the normal part reaches the reference receiver 5 with attentuated intensity. The other part of the radiation beam is reflected at point 13 and received at a defect detection probe 6 which detects the defect 9. The arrow labeled reference numeral designation 16 indicates the direction in which the vibration lead probes (4, 5, 6) can be laterally rotated on support plate 7. From the comparison between the intensity of the radiation beam incident at the reference probe 5 and at the defect detection probe 6 information can be obtained on the size and type of the defect 9.

Figure 2:
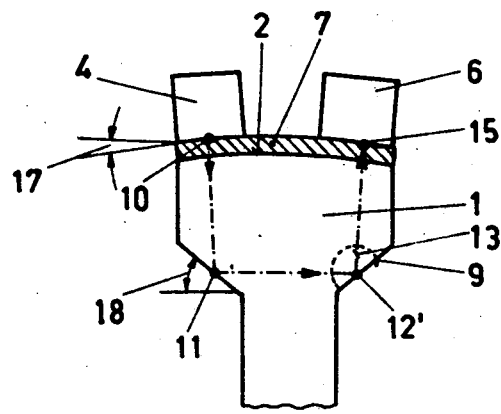
FIG. 2 is a front view of a part of the rotor.

FIG. 2 shows a front view of the middle rotor tooth 1 shown in FIG. 1. As above noted, the reference numbers from FIG. 1 apply to the same parts in FIG. 2, as also in the remaining drawings. In the drawing, the fit of the support plate 7 to the crest 2 of the rotor tooth 1 and also the course of the radiation beam emitted by the transmit probe 4 are readily seen, the position of the ultrasonic beam being shown for the case where a defect 9 is present in the path of the ultrasonic beam. The defect is signalled by the defect detection probe 6, in accordance with the description of FIG. 1. It is to be understood that, in this case, the reference probe 5, not shown in FIG. 2 because it is hidden by the defect detection probe 6, again receives the acoustic beam at reduced intensity.

The curvature of the crest 2 of the rotor tooth 1 and, correspondingly, also of the support plate 7 is shown by the angle 17.

The reference number 18 designates the flank angle of the rotor tooth 1. The probes 4, 5 and 6 are adjusted in such a manner that they are adapted to the angles 17 and 18, that is to say that the sound is directed and the sound is reflected at the tooth flanks of the rotor teeth 1 in the manner described in FIG. 1. The point of emergence 10 of the acoustic beam axis from the transmit probe 4, the reflection at the points 11' and 12' at the two tooth flanks, the reflection 13 at the defect 9 and the entry at point 15 into the defect detection receiver are identical to the process described in FIG. 1.

The subsequent FIGS. 3, 4, 5 and 6 show a top view of different probe arrangements used in accordance with the invention.

Figure 3:
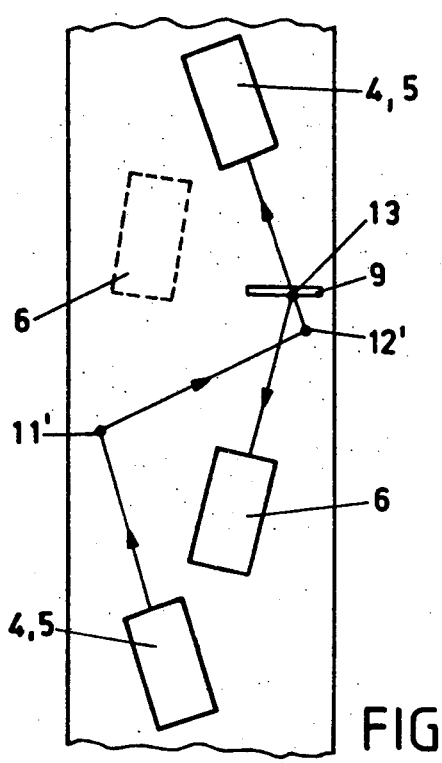
FIGS. 3, 4, 5 and 6 are top views of probe arrangements according to the invention.
Figure 4:
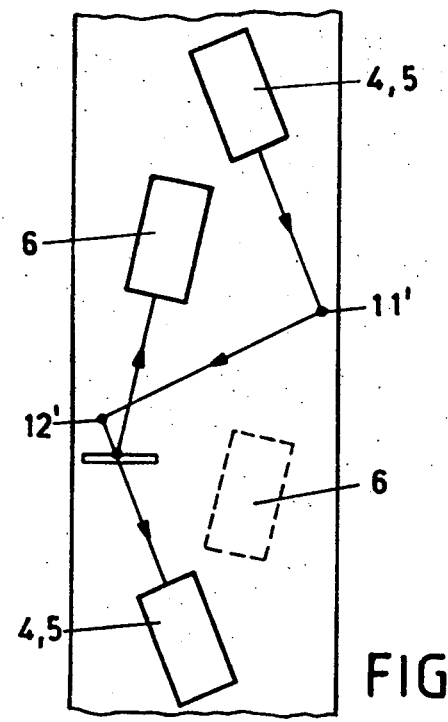

The probe arrangements according to FIGS. 3 and 4 have been drawn separately only because of better clarity of the acoustic beam paths and in each case represent defect detection for only one tooth flank.

For the testing of rotor teeth in accordance with the invention, the two probe arrangements shown in FIGS. 3 and 4 are combined on one support plate 7 and act in conjunction with each other in a manner described below in greater detail.

It can be seen that three probes are required for testing only one tooth flank, and that both tooth flanks can be simultaneously tested by adding a single further probe.

In FIGS. 3 and 4, the acoustic beam is in each case emitted by the transmit probe 4 and the beam axis is then reflected the first time at 11' at the tooth flank which is not being tested and the second time at 12' at the tooth flank which is being tested. The radiation beam is now in each case split by a defect 9 so that the normal path in each case reaches the reference receiver 5 with attenuated intensity. The other part of the radiation beam is in each case reflected at point 13 and in each case received in a defect detection probe 6 which in each case detects the defect 9.

If the processes which have just been described for FIGS. 3 and 4, are considered in a combined action it can be seen that, although the transmit probe 4 and the reference probe 5 are arranged spatially at a distance from one another in the longitudinal and circumferential directions of the rotor, they nevertheless form one functional unit and that the transmit probe 4 and the reference probe 5 act in conjunction with each other in such a manner that each probe works alternately as a transmitter or as a receiver.

Figure 5:
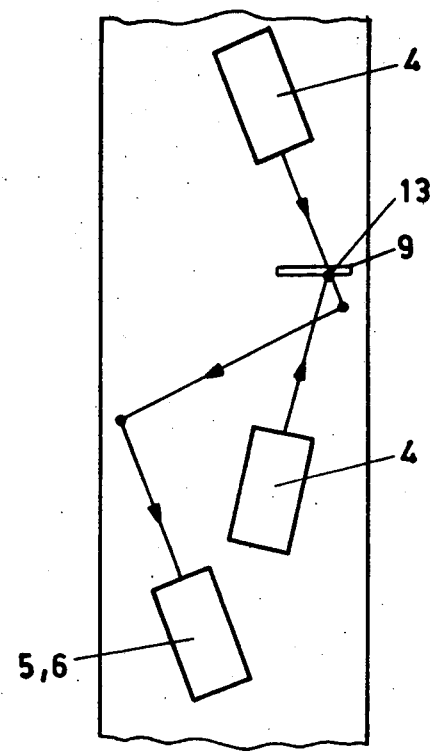

FIG. 5 shows another embodiment of the probe arrangement, one reference probe 5 and one defect detection probe 6 forming one probe unit which works in conjunction with two transmit probes, the probe unit and the two transmit probes 4 being arranged spatially at a distance from one another in the longitudinal and circumferential directions of the rotor. For the sake of simplicity, FIG. 5 only shows the testing of the right-hand tooth flank.

With the probe arrangement shown in FIG. 5, the function of defect or reference signal reception is achieved in a manner analogous to that shown in FIGS. 3 and 4.

Figure 6:
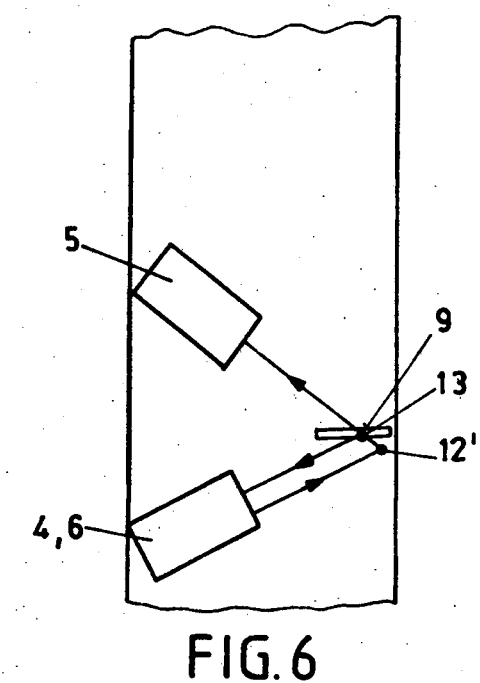

FIG. 6 shows another embodiment of a probe arrangement having only two probes which, however, can be used only for teeth with a special shape and which has a less favorable signal/noise ratio. In this arrangement, the transmit probe 4 and the defect detection probe 6 form one probe unit which works in conjunction with one reference probe, the probe unit and the reference probe 5 being arranged spatially at a distance from one another in the longitudinal and circumferential direction.

Figure 7:
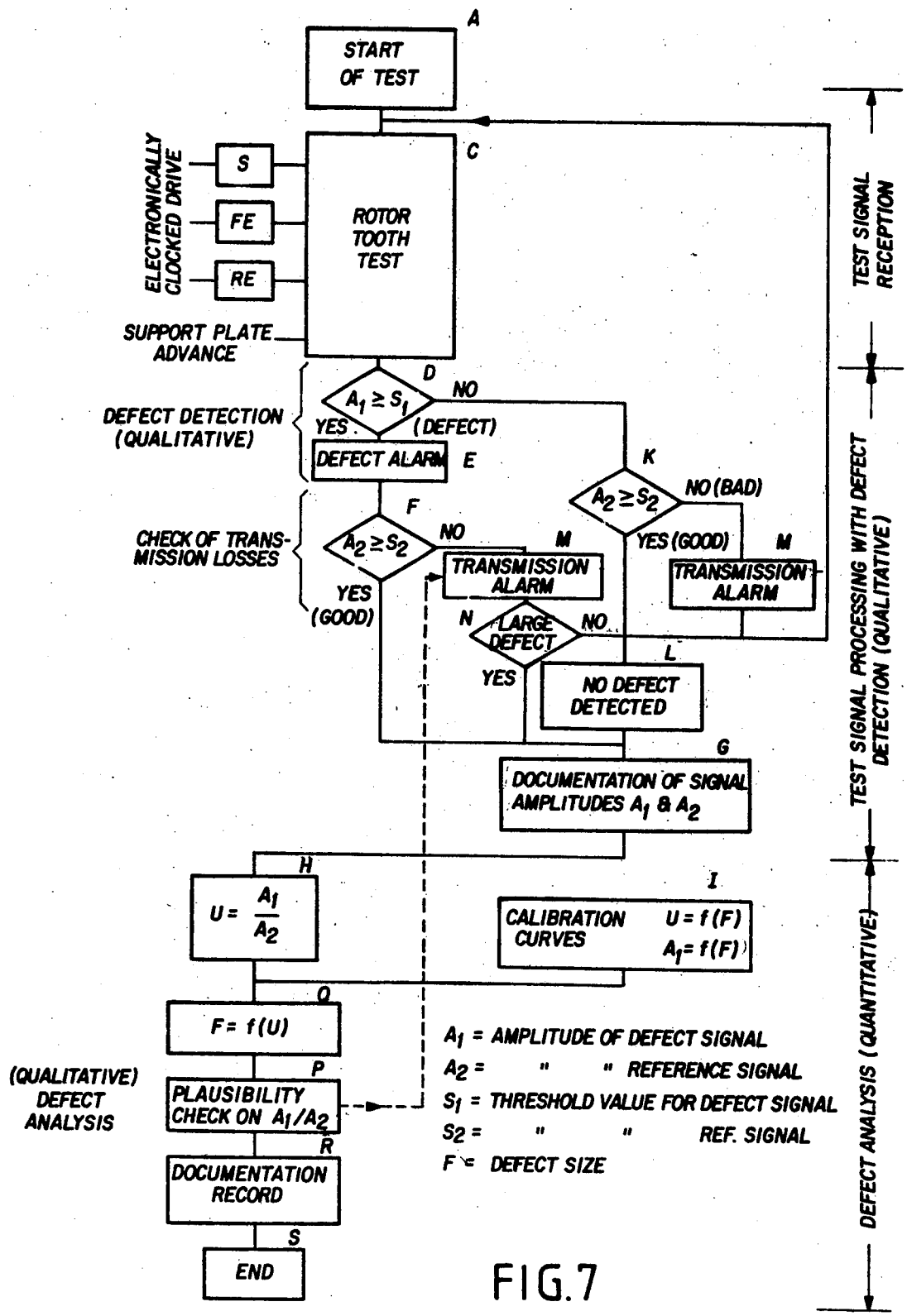
FIG. 7 is a flow chart of a process cycle of a test operation according to the invention.

FIG. 7 shows the individual operational steps of the flow of the process of rotor tooth testing.

Reference A designates the point in the flow diagram at which the start of testing begins after all parts of the test installation have been checked for their operational readiness.

The electronically clocked drive system causes transmit pulses to be radiated by the transmit probe 4 which during the rotor tooth test G in step C are received as receive pulses by the reference probe 5 and, in the case of existence of defects, also by the defect detection probe 6. The rotor tooth test takes place by continuously advancing the support plate which can be carried out manually or mechanically and which extends over the total axial length of the rotor tooth.

In a first test stage, any existing defects are detected qualitatively. This is done in the test step designated by reference D by comparing the amplitude of the defect signal $A_1$ with that of the permissible threshold value of the defect signal $S_1$. The permissible threshold value $S_1$ of the defect signal has been empirically determined and selected in such a way that it is somewhat higher than the amplitude of the background noise signals which originate from harmless irregularities in the wedge support areas and thus indicates that there is no defect in the rotor tooth within a certain type of amplitude of the permissible threshold value $S_1$.

In test step D, two measured results can be alternatively seen:

1D: If $A_1$ is smaller than $S_1$, no defect appears to be present; and

2D: If $A_1$ is greater than $S_1$, a defect exists in principle and a defect alarm follows in step E.

The two alternative measured results as per 1D and 2D must now be subjected to a check for transmission losses which is carried out in the subsequent test steps K and F. If first the measured result according to 1D is considered, in step K again a comparison between the amplitudes of reference signal $A_2$ and the threshold value for the reference signal $S_2$ is carried out.

The permissible threshold values $S_2$ of the reference signal has again been empirically determined and indicates that above a certain amplitude of the permissible threshold value $S_2$ the acoustic transmission from and to the probes 4, 5 and 6 is without problems within the range of fluctuations expected and that no unacceptable losses exist as a result of high wedge contact pressure or as a result of insufficient contact between the support plate 7 and the crest 2 of the rotor tooth 1.

In the test step K, again two measured results can be alternatively seen:

1K: If $A_2$ is greater than $S_2$, this is the normal case, there are no defects in the rotor tooth and the prerequisite for the acoustic transmission to be in order has also been met; and 2K: If $A_2$ is smaller than $S_2$, transmission losses exist.

As has already been mentioned, the case under number 1K represents the normal case of the test in which no defects are detected in the rotor tooth (step L) after the transmission check. The two signal amplitudes $A_1$ and $A_2$ of the test which indicate that the rotor teeth are without defects are finally documented in step G.

If, however, transmission losses are detected in case 2K, a transmission alarm is triggered in step M which leads back to step A where testing of the rotor tooth sections concerned is started again after corrective measures indicated, such as improving the probe-to-specimen contact or increasing the signal amplification, have been carried out.

If now the above-mentioned measured result according to number 2D is considered, in step F (analogously to phase K) the amplitudes $A_2$ and $S_2$ are compared and two measured results can alternatively become apparent:

1F: If $A_2$ is smaller than $S_2$, transmission losses exist which in this case can also be caused by the defect itself so that in step M a transmission alarm is also given but either leads back to step A for further clarification or, with a plausible reduction of $A_2$, to step G only after the appropriate decision has been made in step N; and 2F: If $A_2$ is greater than $S_2$, the acoustic transmission is in order.

A plausible reduction of $A_2$ can exist if due to large-area defects the obscuration of the normal acoustic beam becomes great enough for the amplitude $A_2$ of the reference signal to drop below the threshold value $S_2$, taken into consideration in the calibration curves described subsequently to step I, so that the decision to be made in step N can be made by carrying out a comparison with these curves. It can be seen that the plausibility check of $A_1/A_2$, which in the practical process is simultaneously possible but for reasons of clarity has been shown to occur only in step P, can also supply the information required for this decision.

In step G the two signal amplitudes $A_1$ and $A_2$ are documented. Naturally, this documentation includes not only the two signal amplitudes but, in addition, the rotor tooth section concerned in which these signals were determined.

Subsequently to the qualitative defect detection the quantitative defect analysis takes place in step O by way of forming the quotients from the amplitudes of the defect signal $A_1$ and the reference signal $A_2$ in step H, two so-called calibration curves determined in step I being used as a basis.

These calibration curves represent the functional relationship between defect size and signal amplitudes which was obtained with the aid of defects of known dimensions and incidentally also covers the noticeable relationship between the reference signal $A_2$ and the defect size in the case of larger defects. Monitoring of the transmission losses, which in this area can no longer be done via the threshold value $S_2$, requires the check of amplitudes $A_1$ and $A_2$, taking place in step P, for maintenance of the combinations permissible according to the calibration curves and means, that if non-plausible pairs of values occur a transmission alarm will be triggered followed by a return to step N, whereas with a positive result the defect size determined is documented in the listing in step R.

The test process comes to a conclusion in step S after all rotor teeth have been tested in the longitudinal and circumferential direction of the rotor.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the non-destructive ultrasonic testing of the material of generator rotor teeth provided with an inserted slot wedge, using at least one transmit probe and at least one receive probe, each rotor tooth having first and second opposed flanks, comprising:
   radiating and directing an ultrasonic beam by means of the transmit probe such that the beam is firstly reflected at one tooth flank and then at the opposite flank of the same rotor tooth;
   receiving and signalling the acoustic beam reflected from the opposite tooth flank by means of a reference probe;
   placing a defect detecting probe outside the range of reception of the normally reflected ultrasonic beam in the absence of a defect;
   receiving an ultrasonic beam reflected by any existing defects by means of said defect detection probe; and
   detecting location on any defect based on signals received by the reference probe and the defect detection probe.
2. A process as claimed in claim 1 comprising:
   detecting the extent and orientation of the defects by comparing the signals from the reference probe and the defect detection probe.
3. A process as claimed in claim 1 comprising:
   providing first, second, third and fourth probes;
   firstly transmitting from said first probe to said second probe using said second probe as said reference probe and said third probe as said defect detecting probe;
   secondly transmitting from said second probe to said first probe using said first probe as said reference probe and said fourth probe as said defect detecting probe; and
   controlling the steps of firstly and secondly transmitting in sequence based on the period of signals emitted by a clock generator.
4. A process as claimed in claim 3, comprising:
   associating defect detection in said opposed tooth flanks with said third and fourth probes.
5. A process as claimed in claim 1, comprising:
   rotating the probes out laterally to match to the flank angles and crest angles and thus also the width of the rotor teeth.

* * * * *